United States Patent [19]

Oka et al.

[11] 4,255,444
[45] Mar. 10, 1981

[54] 4-HYDROXY-2-PYRONE DERIVATIVES HAVING ANTIHYPERLIPAEMIC ACTIVITY

[75] Inventors: Hidehiko Oka; Akira Terahara; Akira Endo, all of Hiromachi, Japan

[73] Assignee: Sankyo Company Limited, Tokyo, Japan

[21] Appl. No.: 88,621

[22] Filed: Oct. 26, 1979

[30] Foreign Application Priority Data

Oct. 30, 1978 [JP] Japan ................. 53-133406

[51] Int. Cl.³ ................. C07D 309/30; A61K 31/365
[52] U.S. Cl. ................. 424/279; 260/343.5
[58] Field of Search ................. 260/343.5; 424/279

[56] References Cited

U.S. PATENT DOCUMENTS 3,983,140  9/1976  Endo et al. ................. 260/343.5

Primary Examiner—Henry R. Jiles
Assistant Examiner—Jane T. Fan
Attorney, Agent, or Firm—Frishauf, Holtz, Goodman & Woodward

[57] ABSTRACT

4-Hydroxy-2-pyrone derivatives of formula (I):

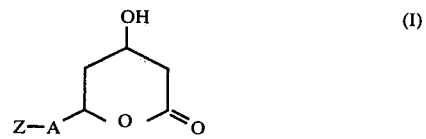

(wherein A represents an alkylene group which is optionally alkyl-substituted or an alkenylene group, and Z represents a substituted or unsubstituted aryl or aryloxy group) may be prepared by cyclizing an ester of formula (II):

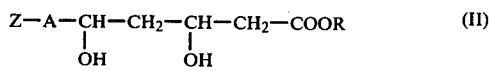

(wherein A and Z are as defined above and R represents an organic group) and have valuable antilipaemic activities.

27 Claims, No Drawings

4-HYDROXY-2-PYRONE DERIVATIVES HAVING ANTIHYPERLIPAEMIC ACTIVITY

BACKGROUND TO THE INVENTION

It is currently believed that a causitive factor in diseases such as atherosclerosis and hyperlipaemia is the deposition of cholesterol in the body, particularly within the arteries. A number of compounds are available for reducing the deposition of cholesterol, including clofibrate and simfibrate. Also, our U.S. Pat. application No. 576,651, filed May 12, 1975, now U.S. Pat. No. 3,983,140 issued Sept. 28, 1976, discloses a series of compounds (designated ML-236A, ML-236B and ML-236C) which are 4-hydroxy-2-pyrone derivatives. There is, however, a continuing need for new compounds having this activity.

BRIEF SUMMARY OF INVENTION

We have now discovered that certain other 4-hydroxy-2-pyrone derivatives are highly effective in inhibiting the synthesis of cholesterol, thus lowering cholesterol and lipid levels in the blood and liver. By virtue of their potent hypocholesteraemic and hypolipaemic activities, these compounds are suitable for treatment of diseases such as hyperlipaemia.

Accordingly, the invention provides compounds of formula (I):

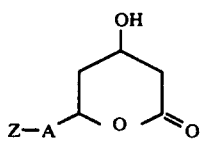

(wherein:
A represents an alkylene group optionally alkyl-substituted or an alkenylene group; and
Z represents a substituted or unsubstituted aryl or aryloxy group).

The invention also provides a process for the preparation of compounds of formula (I) by the cyclization with an alkali of a compound of formula (II):

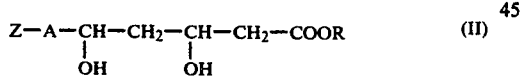

(wherein A and Z are as defined above and R represents an organic group). The compounds of formula (II) may themselves be prepared by reacting a compound of formula (III):

(wherein A and Z are as defined above) with a dianion of an acetoacetic ester and reducing the resulting compound.

The invention still further provides a pharmaceutical preparation which comprises, as active ingredient, at least one 4-hydroxy-2-pyrone derivative of formula (I), together with a pharmaceutically acceptable carrier or excipient.

DETAILED DESCRIPTION OF INVENTION

In the above compounds, where A represents an alkylene group optionally substituted by a alkyl group, it is preferably a $C_1$ or $C_2$ alkylene group optionally substituted with a $C_1$–$C_3$ alkyl group. Preferred examples of such groups represented by A are the methylene, ethylene, methylethylene and dimethylmethylene groups. Where A represents an alkenylene group, this is preferably a $C_2$ or $C_3$ alkenylene group and most preferably a vinylene group or a propenylene group.

Where Z represents an aryl group, this is preferably a phenyl group, a naphthyl group or a tetrahydronaphthyl (e.g. 5,6,7,8-tetrahydro-1-naphthyl) group. Where the aryl group is substituted, the substituents are preferably one or more halogen atoms and/or $C_1$–$C_3$ alkyl groups, preferably chlorine atoms or methyl groups. Preferred examples of such substituted aryl groups are o-chlorophenyl, m-chlorophenyl, p-chlorophenyl, 2,4-dichlorophenyl, 3,5-dichlorophenyl, 2,6-dichlorophenyl, 2-methyl-1-naphthyl, and 2-methyl-5,6,7,8-tetrahydro-1-naphthyl groups. Where Z represents an aryloxy group, this is preferably a phenoxy group or a naphthoxy group. Where the aryloxy group is substituted, the substituents are preferably one or more halogen, particularly chlorine atoms. Preferred substituted aryloxy groups are o-chlorophenoxy, m-chlorophenoxy, p-chlorophenoxy, 2,4-dichlorophenoxy, 3,5-dichlorophenoxy and 2,6-dichlorophenoxy groups.

Representative examples of compounds of formula (I) are given below. The compounds are hereafter identified by the numbers assigned to them in the following list.

1. 4-Hydroxy-6-[2-(2-methyl-1-naphthyl)ethyl]-3,4,5,6-tetrahydro-2H-pyran-2-one.
2. 4-Hydroxy-6-(1-phenoxyethyl)-3,4,5,6-tetrahydro-2H-pyran-2-one.
3. 4-Hydroxy-6-[2-(1-naphthyl)ethyl]-3,4,5,6-tetrahydro-2H-pyran-2-one.
4. 6-[1-(4-Chlorophenoxy)-1-methylethyl]-4-hydroxy-3,4,5,6-tetrahydro-2H-pyran-2-one.
5. 6-[2-(2,6-dimethyl-1-naphthyl)ethyl]-4-hydroxy-3,4,5,6-tetrahydro-2H-pyran-2-one.
6. 4-Hydroxy-6-[2-(2-methyl-5,6,7,8-tetrahydro-1-naphthyl)ethyl]-3,4,5,6-tetrahydro-2H-pyran-2-one.
7. 4-Hydroxy-6-[1-(2-methylphenyl)ethyl]-3,4,5,6-tetrahydro-2H-pyran-2-one.
8. 6-[1-(2,6-Dimethylphenyl)ethyl]-4-hydroxy-3,4,5,6-tetrahydro-2H-pyran-2-one.
9. 6-[1-(2-Chlorophenyl)ethyl]-4-hydroxy-3,4,5,6-tetrahydro-2H-pyran-2-one.
10. 6-[1-(2,6-Dichlorophenyl)ethyl]-4-hydroxy-3,4,5,6-tetrahydro-2H-pyran-2-one.
11. 4-Hydroxy-6-[3-(2-methyl-1-naphthyl)propyl]-3,4,5,6-tetrahydro-2H-pyran-2-one.
12. 4-Hydroxy-6-[3-(1-naphthyl)propyl]-3,4,5,6-tetrahydro-2H-pyran-2-one.
13. 4-Hydroxy-6-(1-phenylethyl)-3,4,5,6-tetrahydro-2H-pyran-2-one.
14. 6-[1-(4-Chlorophenyl)ethyl]-4-hydroxy-3,4,5,6-tetrahydro-2H-pyran-2-one.

The 4-hydroxy-2-pyrone derivatives of formula (I) may be prepared by the cyclization of a 3,5-dihydroxypentanoic ester derivative of formula (II), as defined above. This cyclization may be conducted by treating the 3,5-dihydroxypentanoic ester derivative of formula (II) with an alkali. However, the preferred method is to treat the compound of formula (II) with an alkali, preferably an alkali metal hydroxide (e.g. sodium hydroxide or potassium hydroxide), followed by a mineral acid (e.g. hydrochloric acid or sulphuric acid). The reaction may be carried out in the presence or absence of a solvent, the nature of which is not critical, provided that it has no adverse effect upon the reaction. Preferred solvents are water-immiscible organic solvents, such as ketones (e.g. acetone or methyl ethyl ketone) or ethers (e.g. tetrahydrofuran or dioxane). The reaction temperature is also not particularly critical and, for convenience, we prefer to operate either at ambient temperature or at the reflux temperature of the solvent employed.

Preferred 3,5-dihydroxypentanoic ester derivatives (II) are those in which R represents a $C_1$-$C_4$ alkyl group, especially an ethyl group. These compounds form the subject of our copending Application Ser. No. 88,619, filed Oct. 26, 1979, entitled "3,5-Dihydroxypentanoic ester derivatives having antihyperlipaemic activity."

The 3,5-dihydroxypentanoic ester derivatives of formula (II) may be prepared by reacting a dianion of an acetoacetic ester with an aldehyde of formula (III)

Z—A—CHO    (III)

(wherein Z and A are as defined above). The dianion may be prepared from the acetoacetic ester by known means.

This reaction may be summarized by the following reaction scheme:

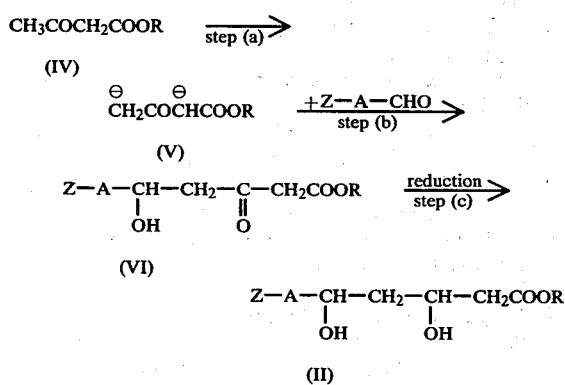

Step (a)

The conversion of the acetoacetic ester (IV) to dianion (V) may be effected by adding sodium hydride or metallic sodium in an anhydrous aprotic polar solvent to a solution of the acetoacetic ester (IV) in an anhydrous aprotic polar solvent, under ice-cooling, stirring the resulting mixture, usually at a temperature of from −5° C. to −10° C., for 30–60 minutes, and then adding an alkyllithium (e.g. n-butyllithium), an aryllithium (e.g. phenyllithium), potassium t-butoxide or lithium diisopropylamide thereto. Examples of suitable aprotic polar solvents are diethyl ether, diisopropyl ether, diisobutyl ether, dioxane and tetrahydrofuran, of which tetrahydrofuran is preferred. It is customary and preferred to use the acetoacetic ester (IV) and the other reagents in equimolar amounts.

Alternatively, this reaction may be carried out using one mole of the acetoacetic ester (IV) and 2 moles of the alkyllithium, aryllithium, potassium t-butoxide or lithium diisopropylamide, but without employing the sodium hydride or metallic sodium.

The acetoacetic ester dianion (V) thus formed in situ may be employed as such in the subsequent reaction without intermediate isolation or purification.

Step (b)

The conversion of the acetoacetic ester dianion (V) to the compound (VI) is effected by adding the aldehyde Z—A—CHO, with ice-cooling, to a reaction mixture containing the dianion (V) after stirring for a while with cooling. The reaction mixture is then stirred for a short time and then the whole mixture is poured into ice-water and acidified with a mineral acid (e.g. hydrochloric or sulphuric acid), thereby forming the desired compound of formula (VI). This compound may be recovered from the reaction mixture by conventional means, for example by extracting with a suitable organic solvent (e.g. ethyl acetate), drying over anhydrous sodium sulphate and then evaporating off the solvent under reduced pressure. The isolated product may, if desired, be further purified by conventional means, for example by silica gel column chromatography eluted with a mixture of benzene and ethyl acetate.

Step (c)

The conversion of the compound of formula (VI) to the 3,5-dihydroxypentanoic ester (II) may be effected be reducing the compound (VI), e.g. with sodium borohydride in an absolute alcohol (e.g. methanol or ethanol) under ice-cooling and then treating the reaction mixture with a mineral acid (e.g. hydrochloric acid or sulphuric acid). After completion of the reaction, the 3,5-dihydroxypentanoic ester (II) may be recovered by conventional means, for example by extracting the reaction mixture with a suitable organic solvent (e.g. ethyl acetate), drying the extract over anhydrous sodium sulphate and then evaporating off the solvent under reduced pressure. The isolated product may be further purified by conventional means, for example by silica gel column chromatography eluted with a mixture of benzene and ethyl acetate.

Although intermediate isolation and purification of the intermediate compounds (VI) and (II) is desirable, in some cases, these intermediates may be used without isolation or without further purification to give the desired final product (I). This final product may, after completion of the reaction, be recovered from the reaction mixture by conventional means, for example by extracting with a suitable organic solvent (e.g. ethyl acetate), drying the extract over anhydrous sodium sulphate and then evaporating off the solvent under reduced pressure. The isolated compound may be further purified by conventional means, for example by silica gel column chromatography eluted with a mixture of benzene and ethyl acetate or by preparative thin layer chromatography developed with a mixture of benzene and ethyl acetate.

The biological activity of compounds of the invention was demonstrated by the following test.

Crude enzyme extracted from rat liver was reacted with radioactive acetic acid at 37° C. for 60 minutes. The radioactive cholesterol thus biosynthesized was saponified and precipitated with digitonin, and the radioactivity was measured to determine the amount of cholesterol produced. The reaction was repeated, but adding one of the compounds of the invention listed in the following Table at the beginning of the reaction, and the amount of cholesterol biosynthesized was again determined, to give a quantitative measurement of the inhibitory effect of the compounds of the invention. The concentrations (μg/ml) of the compounds of the invention and of a known compound (clofibrate) which gave approximately 50% inhibition of cholesterol biosynthesis are reported in the following Table as $I_{50}$ values [see Bricker et al, The Journal of Biological Chemistry, 247, 4914 (1972)]. The compounds of the invention are identified in the following Table by the numbers heretofore assigned to them.

TABLE

| Compound No. | $I_{50}$ (μg/ml) |
|---|---|
| 1 | 0.75 |
| 2 | 42.3 |
| 3 | 6.4 |
| 4 | 21.3 |
| Clofibrate | 250–300 |

The foregoing results demonstrate that the compounds of the invention are potent inhibitors of cholesterol biosynthesis and have low toxicity. They are, therefore, useful as pharmaceuticals for the treatment of such diseases as hyperlipaemia.

The compounds of the invention can be administered orally, by intravenous injection or by any other conventional means and they are preferably formulated with carriers or diluents, e.g. as is well-known for known antihyperlipaemic agents such as clofibrate or simfibrate. The posology is dependent upon the age, body weight and condition of the patient, but the daily dosage for adults is generally from 500 to 5,000 mg/day, more preferably about 2,000 mg/day, conveniently administered in divided doses three or four times a day.

The pharmaceutical preparation of the invention is desirably provided in a form suitable for adsorption in the gastrointestinal tract. Tablets and capsules for oral administration are normally in unit dosage form and contain conventional vehicles, for example: binding agents, such as syrup, gum arabic, gelatin, sorbit, gum tragacanth or polyvinylpyrrolidone; excipients, such as lactose, sucrose, corn starch, calcium phosphate, sorbitol or glycine; lubricants, such as magnesium stearate, talc, polyethylene glycol or silica, disintegrating agents, such as potato starch; or wetting agents, such as sodium lauryl sulphate. Tablets may be coated by any method well-known in the art. Liquid preparations for oral administration may be in the form of aqueous or oily suspensions, solutions, syrups, elixirs or the like or they may be in dried form for redissolution in water or another suitable vehicle. Such liquid preparations may comprise conventional additives, for example suspending agents, such as sorbit syrup, methylcellulose, glucose/sugar syrup, gelatin, hydroxyethylcellulose, carboxymethylcellulose, aluminum stearate gel or a hydrogenated edible fat; emulsifying agents, such as lecithin, sorbitan monoleate or gum arabic; non-aqueous vehicles, such as almond oil, fractionated coconut oil, oily esters, propylene glycol or ethanol; or preservatives, such as methyl p-hydroxybenzoate, propyl p-hydroxybenzoate or sorbic acid.

Injectable preparations are preferably provided in the form of unit dosage ampoules or in multiple dosage vessels with added preservatives. These preparations may be in the form of suspensions, solutions or emulsions in oily or aqueous vehicles and may also comprise conventional additives, for example suspending agents and/or stabilizers and/or dispersing agents (such as those exemplified above). Alternatively, the active ingredient may be in the form of a powder which can be redissolved in a suitable vehicle, e.g. pyrogen-free sterilized water, at the time of use.

The pharmaceutical preparations of the invention preferably contain not less than 0.1% by weight, more preferably from 10 to 60% by weight, of the active ingredient, depending upon the route of administration. A unit dosage form of the preparation preferably contains from 50 to 500 mg of the active ingredient.

The invention is further illustrated by the following Examples, which describe the preparation of certain of the compounds of the invention.

EXAMPLE 1

4-Hydroxy-6-(1-phenoxyethyl)-3,4,5,6-tetrahydro-2H-pyran-2-one (Compound No. 2)

(a) 13 g (0.1 mole) of ethyl acetoacetate in 30 ml of anhydrous tetrahydrofuran were added drop by drop to a 50% w/w suspension in oil of 4.8 g (0.1 mole) of sodium hydride in 100 ml of anhydrous tetrahydrofuran, with ice-cooling and stirring. The mixture was stirred for a further 30 minutes and then cooled to a temperature from $-10°$ C. to $-5°$ C. To the mixture was added dropwise 70 ml of an n-hexane solution containing 0.1 mole of n-butyllithium. The mixture was stirred at a temperature from $-5°$ C. to $0°$ C. for 30 minutes to produce the dianion of ethyl acetoacetate and was then cooled to $-40°$ C.

9 g (0.06 mole) of 2-phenoxypropionaldehyde in 30 ml of anhydrous tetrahydrofuran were added all at once to the reaction mixture. After stirring for 30 minutes, the whole reaction mixture was poured into about 1 liter of ice-water. The resulting mixture was acidified by the addition of sulphuric acid and then extracted three times, each time with 200 ml of ethyl acetate. The combined extracts were dried over anhydrous sodium sulphate and then the solvent was evaporated off under reduced pressure. The resulting residue was adsorbed on a silica gel chromatography column and eluted with a 98:2 by volume mixture of benzene and ethyl acetate, to give 5.7 g (yield 33.9%) of ethyl 5-hydroxy-3-oxo-6-phenoxyheptanoate, in the form of an oil.

(b) To 2.5 g (0.006 mole) of sodium borohydride in 30 ml of absolute ethanol was added dropwise 30 ml of an absolute ethanol solution containing 3.5 g (0.0135 mole) of the ethyl 5-hydroxy-3-oxo-6-phenoxyheptanoate obtained in step (a). After completion of the addition, cooling was immediately stopped and the mixture was allowed to warm to room temperature and was stirred for about 40 minutes.

To the reaction mixture were then added about 300 ml of ice-water and the mixture was then acidified by the addition of 2 N sulphuric acid. After saturating the solution with sodium chloride, it was extracted three times, each time with 50 ml of ethyl acetate. The combined extracts were dried over anhydrous sodium sulphate and then the solvent was evaporated off, to give 1.3 g (yield 37%) of ethyl 3,5-dihydroxy-6-phenoxyheptanoate.

(c) To a solution of 1.3 g (0.0046 mole) of ethyl 3,5-dihydroxy-6-phenoxyheptanoate obtained as described in step (b) above in 20 ml of acetone were added 10 ml of a 15% w/w aqueous solution of potassium hydroxide and then the mixture was stirred at room temperature for 20 hours. The mixture was then acidified with hydrochloric acid and extracted three times, each with 10 ml of ethyl acetate. The extracts were combined, washed with saturated aqueous sodium chloride and dried over anhydrous sodium sulphate. The solvent was then evaporated off under reduced pressure and the resulting residue was adsorbed on a silica gel preparative thin layer chromatograph and eluted with a 2:1 by volume mixture of the benzene and ethyl acetate, giving 200 mg of the desired Compound No. 2.

Nuclear Magnetic Resonance Spectrum (CDCl$_3$) δ ppm:
1.2 (doublet, J=5 cps, 3H, —CHC$\underline{H}_3$ at 6-position);
2.45 (doublet, J=4 cps, 2H, H$_2$ at 3-position);
3.47–4.8 (multiplet, 3H, H$_2$ at 5-position and H at 6-position);
6.6–7.3 (multiplet, 5H, C$_6$H$_5$).

Infrared Absorption Spectrum (Nujol-Trade Mark) $\nu_{max}$ cm$^{-1}$:
1740 (C=O at 2-position);
3400 (OH at 4-position).

Thin layer chromatography (silica gel, developed with a 2:1 by volume mixture of benzene and ethyl acetate) R$_f$ value=0.2.

EXAMPLE 2

6-[1-(4-Chlorophenoxy)-1-methylethyl]-4-hydroxy-3,4,5,6-tetrahydro-2$\underline{H}$-pyran-2-one (Compound No. 4)

10 g (0.0354 mole) of ethyl 6-(p-chlorophenoxy)-6-methyl-5-hydroxy-3-oxoheptanoate [prepared from 2-(p-chlorophenoxy)-2-methylpropanal according to the procedure of step (a) of Example 1] were reduced with 0.8 g (0.021 mole) of sodium borohydride in 100 ml of ethanol, with ice-cooling and stirring. The residue obtained from the reaction mixture by the procedure described in Example 1 was dissolved, without purification, in 50 ml of acetone, and then 100 ml of a 15% w/w aqueous solution of potassium hydroxide was added. The mixture was then stirred at room temperature for 20 hours, after which it was acidified with hydrochloric acid and extracted three times, each time with 100 ml of ethyl acetate. The combined extracts were dried over anhydrous sodium sulphate and then the solvent was evaporated off under reduced pressure. The residue was adsorbed on a silica gel chromatography column and fractions eluted with a 1:5 by volume mixture of benzene and ethyl acetate were evaporated to dryness to give 2.6 g (yield 30%) of the desired Compound No. 4. This was recrystallized to give colourless crystals melting at 72°–76° C.

Elemental Analysis:
Calculated for C$_{14}$H$_{17}$O$_4$Cl:
C, 59.06%; H, 6.0%; Cl, 12.45%.
Found: C, 59.53%; H, 6.0%; Cl, 12.31%.

Nuclear Magnetic Resonance Spectrum (CDCl$_3$) δ ppm:
1.3 [singlet, 6H, C(CH$_3$)$_2$ at 6-position];
2.7 (doublet, J=4 cps, 2H,H$_2$ at 3-position);
4.1–4.6 (multiplet, 1H, H at 4-position);
4.1–4.6 (multiplet, 2H, H$_2$ at 5-position);
4.7 (double doublet, 1H, H at 6-position)
7.1 (quartet, 4H, C$_6$H$_4$).

Infrared Absorption Spectrum (Nujol) $\nu_{max}$cm$^{-1}$:
1700 (C=O).

Following the procedures of Examples 1 and 2, the following compounds were also prepared:

Compound No. 1

4-Hydroxy-6-[2-(2-methyl-1-naphthyl)ethyl]-3,4,5,6-tetrahydro-2$\underline{H}$-pyran-2-one Thin layer chromatography (silica gel, developed with 2:1 by volume benzene and ethyl acetate) R$_f$ value=0.3.

Compound No. 3

4-Hydroxy-6-[2-(1-naphthyl)ethyl]-3,4,5,6-tetrahydro-2$\underline{H}$-pyran-2-one Thin layer chromatography (silica gel, developed with 2:1 by volume benzene and ethyl acetate) R$_f$ value=0.3.

We claim:
1. A compound of formula (I):

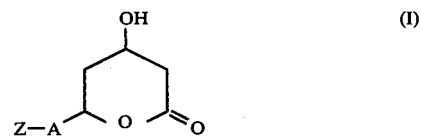

wherein
A represents a C$_1$–C$_2$ alkylene group, a C$_1$–C$_4$ alkylene group having one or more C$_1$–C$_3$ alkyl substituents, or a C$_2$–C$_3$ alkenylene group; and
Z represents an aromatic ring group selected from the group consisting of (i) a phenyl, naphthyl or tetrahydronaphthyl group, (ii) a substituted phenyl, naphthyl or tetrahydronaphthyl group wherein the aromatic ring is substituted with at least one substituent selected from the group consisting of halogen atoms and C$_1$–C$_3$ alkyl groups, (iii) phenoxy or naphthoxy group, and (iv) a substituted phenoxy or naphthoxy group wherein the aromatic ring is substituted with one or more halogen atoms.

2. The compound of claim 1, wherein A represents a C$_1$ or C$_2$ alkylene group or a C$_1$ or C$_2$ alkylene group substituted with a C$_1$–C$_3$ alkyl group.

3. The compound of claim 2, wherein A represents a methylene, ethylene, methylethylene or dimethylmethylene group.

4. The compound of claim 1, wherein A represents a C$_2$ or C$_3$ alkenylene group.

5. The compound of claim 4, wherein A represents a vinylene or propenylene group.

6. The compound of claim 1 or 2 or 4, wherein Z represents a phenyl group, a naphthyl group or a tetrahydronaphthyl group or one of said groups substituted by a halogen atom.

7. The compound of claim 6, wherein Z represents a phenyl, naphthyl or tetrahydronaphthyl group or one of said groups, substituted with a chlorine atom.

8. The compound of claim 1, or 3 or 5, wherein Z represents an o-chlorophenyl, m-chlorophenyl, p-chlorophenyl, 2,4-dichlorophenyl, 3,5-dichlorophenyl, 2,6-dichlorophenyl, 2-methyl-1-naphthyl, or 2-methyl-5,6,7,8-tetrahydro-1-naphthyl group.

9. The compound of claim 1, or 2 or 4, wherein Z represents a phenoxy group or a naphthoxy group or one of said groups substituted with one or more halogen atoms.

10. The compound of claim 1, or 3 or 5, wherein Z represents a o-chlorophenoxy, m-chlorophenoxy, p-chlorophenoxy, 2,4-dichlorophenoxy, 3,5-dichlorophenoxy or 2,6-dichlorophenoxy group.

11. 4-Hydroxy-6-[2-(2-methyl-1-naphthyl)ethyl]-3,4,5,6-tetrahydro-2$\underline{H}$-pyran-2-one of the formula of claim 1.

12. 4-Hydroxy-6-(1-phenoxyethyl)-3,4,5,6-tetrahydro-2H-pyran-2-one of the formula of claim 1.

13. 4-Hydroxy-6-[2-(1-naphthyl)ethyl]-3,4,5,6-tetrahydro-2H-pyran-2-one of the formula of claim 1.

14. 6-[1-(4-Chlorophenoxy)-1-methylethyl]-4-hydroxy-3,4,5,6-tetrahydro-2H-pyran-2-one of the formula of claim 1.

15. 6-[2-(2,6-Dimethyl-1-naphthyl)ethyl]-4-hydroxy-3,4,5,6-tetrahydro-2H-pyran-2-one of the formula of claim 1.

16. 4-Hydroxy-6-[2-(2-methyl-5,6,7,8-tetrahydro-1-naphthyl)ethyl]-3,4,5,6-tetrahydro-2H-pyran-2-one of the formula of claim 1.

17. 4-Hydroxy-6-[1-(2-methylphenyl)ethyl]-3,4,5,6-tetrahydro-2H-pyran-2-one of the formula of claim 1.

18. 6-[1-(2,6-Dimethylphenyl)ethyl]-4-hydroxy-3,4,5,6-tetrahydro-2H-pyran-2-one of the formula of claim 1.

19. 6-[1-(2-Chlorophenyl)ethyl]-4-hydroxy-3,4,5,6-tetrahydro-2H-pyran-2-one of the formula of claim 1.

20. 6-[1-(2,6-Dichlorophenyl)ethyl]-4-hydroxy-3,4,5,6-tetrahydro-2H-pyran-2-one of the formula of claim 1.

21. 4-Hydroxy-6-[3-(2-methyl-1-naphthyl)propyl]-3,4,5,6-tetrahydro-2H-pyran-2-one of the formula of claim 1.

22. 4-Hydroxy-6-[3-(1-naphthyl)propyl]-3,4,5,6-tetrahydro-2H-pyran-2-one of the formula of claim 1.

23. 4-Hydroxy-6-(1-phenylethyl)-3,4,5,6-tetrahydro-2H-pyran-2-one of the formula of claim 1.

24. 6-[1-(4-Chlorophenyl)ethyl]-4-hydroxy-3,4,5,6-tetrahydro-2H-pyran-2-one of the formula of claim 1.

25. An antihyperlipaemic composition comprising as active ingredient an effective amount of a compound of formula (I):

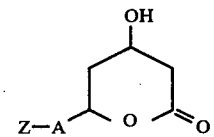

wherein

A represents a $C_1$–$C_2$ alkylene group, a $C_1$–$C_2$ alkylene group having one or more $C_1$–$C_3$ alkyl substituents, or a $C_2$–$C_3$ alkenylene group; and Z represents an aromatic ring group selected from the group consisting of (i) a phenyl, naphthyl or tetrahydronaphthyl group, (ii) a substituted phenyl, naphthyl or tetrahydronaphthyl group wherein the aromatic ring is substituted with at least one substituent selected from the group consisting of halogen atoms and $C_1$–$C_3$ alkyl groups, (iii) phenoxy or naphthoxy group, and (iv) a substituted phenoxy or naphthoxy group wherein the aromatic ring is substituted with one or more halogen atoms in admixture with a pharmaceutically acceptable carrier or excipient.

26. The composition as claimed in claim 25, in a form suitable for oral or parenteral administration.

27. The composition as claimed in claim 25, wherein said compound of formula (I) is selected from the group consisting of:
4-hydroxy-6-[2-(2-methyl-1-naphthyl)ethyl]-3,4,5,6-tetrahydro-2H-pyran-2-one;
4-hydroxy-6-(1-phenoxyethyl)-3,4,5,6-tetrahydro-2H-pyran-2-one;
4-hydroxy-6-[2-(1-naphthyl)ethyl]-3,4,5,6-tetrahydro-2H-pyran-2-one; and
6-[1-(4-chlorophenoxy)-1-methylethyl]-4-hydroxy-3,4,5,6-tetrahydro-2H-pyran-2-one.

* * * * *